United States Patent
Wu et al.

(10) Patent No.: US 9,981,953 B1
(45) Date of Patent: May 29, 2018

(54) CONTRAST AGENT PRECURSOR AND METHOD FOR PREPARING THE SAME

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Wen-Ching Wu, Taoyuan (TW); Kuei-Lin Lu, Taoyuan (TW); Yu Chang, Taoyuan (TW); Cheng-Fang Hsu, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 0 days. days.

(21) Appl. No.: 15/397,998

(22) Filed: Jan. 4, 2017

(51) Int. Cl.
*C07D 403/12* (2006.01)

(52) U.S. Cl.
CPC ................... *C07D 403/12* (2013.01)

(58) Field of Classification Search
CPC .................................................... C07D 403/12
See application file for complete search history.

(56) References Cited

FOREIGN PATENT DOCUMENTS

WO 2009151646 * 12/2009 ............. A61K 51/00

* cited by examiner

*Primary Examiner* — Noble E Jarrell
(74) *Attorney, Agent, or Firm* — Rosenberg, Klein & Lee

(57) ABSTRACT

A contrast agent precursor is revealed. The contrast agent precursor includes a 1,4,7-Tris(carbonylmethyl)-1,4,7,10-tetraazacyclododecane that forms complexes with radioisotopes or connects to a peptide. The contrast agent precursor also includes a 2-nitroimidazole that allows the precursor to become retained in hypoxic tissues According to the features mentioned above, the contrast agent prepared by the precursor has a better binding specificity, labeling accuracy and detection sensitivity. Moreover, a method for preparing the contrast agent precursor not only solves the emulsion problem generated during conventional synthesis of intermediate products but also provides a solution to the problem of residual trifluoroacetic acid. Both the yield rate and the purity of the final product are also improved.

8 Claims, 3 Drawing Sheets taking 1,4,7,10-tetraazacyclododecane to react with tert-butyl bromoacetate and performing a first purification reaction to get 1,4,7-Tris(tert-butoxycarbonylmethyl)-1,4,7,10-tetraazacyclododecane

carrying out a coupling reaction of 1,4,7-Tris(tert-butoxycarbonylmethyl)-1,4,7,10-tetraazacyclododecane with 6-[(2-nitroimidazole)hexyl]chloroacetamide and performing a second purification reaction to get 1,4,7-Tris(tert-butoxycarbonylmethyl) -1,4,7,10-tetraazacyclododecane-10-N-[6-(2-nitroimidazole)hexyl]- acetamide

performing a deprotection reaction of 1,4,7-Tris(tert-butoxycarbonylmethyl) -1,4,7,10-tetraazacyclododecane-10-N-[6-(2-nitroimidazole)hexyl]acetamide and carrying out a thrid purification reaction to get (1,4,7-Tris(carbonylmethyl)-1,4,7,10-tetraazacyclododecane-10-N-[6-(2-nitroimidazole)hexyl]acetamide.

Fig. 3

CONTRAST AGENT PRECURSOR AND METHOD FOR PREPARING THE SAME

BACKGROUND OF THE INVENTION

Field of the Invention

The present invention relates to a contrast agent precursor and a method for preparing the same, especially to a contrast agent precursor, 1,4,7-tris(carbonylmethyl)-1,4,7,10-tetra-azacyclododecane-10-N-(6-(2-nitro-imidazole)-hexyl)acetamide, and a method for preparing the same.

Descriptions of Related Art

Hypoxia is a condition in which the cell or the tissue is not oxygenated adequately, and is defined as $PO_2$ (oxygen partial pressure)<5 mm. Hypoxia plays an important role in the pathology of many human diseases including common feature of stroke, myocardial infarction, cancer, etc.

Take malignant tumors as an example, hypoxia is one of characteristic properties of tumor microenvironment. Hypoxic tumor cells are 3 times more resistant to ionizing radiation than normal well-oxygenated cells. Thus tumor cells are more resistant to radiation therapy. Moreover, under hypoxic conditions, signal transduction in the cell is induced for activation of self-protection mechanism such as accelerated secretion of vascular endothelial growth factor. Thereby the blood oxygen content is increased and angiogenesis is promoted. Thus hypoxia plays a key role in growth and metastasis of tumor cells. Thereby early diagnosis and treatment can prevent malignant progression of the cells.

Nuclear medical imaging is a diagnostic technique that obtains images of organs or tissues in living organisms by radioactive isotopes, such as whole body bone scan and tumor scan. A radioisotope-labeled contrast agent is delivered into the living organism by a non-invasive way. The contrast agent is absorbed by different organs or tissues according to the nuclide type or the labeling method. Then a nuclear medicine camera detects the radiation emitted from the body and takes images of the specific organs or tissues for clinical diagnosis and evaluation.

Chapman proposed the use of radioisotope labeled 2-nitroimidazoles for hypoxia imaging in 1979. The nitro group of 2-nitroimidazoles is reduced into amine in the human body. In normoxic conditions, the amine is rapidly oxidized into nitro group and able to pass through the cell membrane for being transported from the cell. Under hypoxic conditions, the amine of 2-nitroimidazole is unable to pass cell membrane due to increased polarity and is retained in the cell. The cell is radioactive so that the image of the hypoxic tissue is further obtained and is used for diagnosis and treatment of various diseases including stroke, myocardial infarction, cancer, etc.

However, the detection of hypoxic tissues mentioned above still has the problem of specificity. Once the binding specificity of the contrast agent is increased, not only the detection accuracy and sensitivity can be improved, the dose of the contrast agent required can also be reduced for reducing side effects. Thus how to improve the binding specificity of the contrast agent is an important issue.

The use of isotope-labeled peptides is one of the methods that enhance contrast agent specificity. In conventional techniques, the radioactive isotope is directly bonded to the functional group of an amino acid. However, there is a problem of binding efficiency. There is a certain ratio of peptides failed to be labeled in each labeling. This will affect the sensitivity of the following detection. Moreover, each radioisotope has a half-life so that the contrast agent should be immediately injected into the living organism immediately after being prepared. Yet many clinical tests prefer rapid results and the labeling reaction takes too long.

In order to solve the above problems of conventional techniques, there is a need to find out a contrast agent precursor and a method for preparing the same. The contrast agent has a specificity of binding to specific biological molecules of specific tissues and identification of the hypoxic tissue. Besides effective shortening of preparation time, the accuracy and the sensitivity of the contrast agent for enhancing tumor tissue imaging are also improved. The development of the nuclear medicine imaging has been driven by the novel contrast agent.

SUMMARY OF THE INVENTION

Therefore it is a primary object of the present invention to provide a contrast agent precursor that includes a 1,4,7-Tris (carbonylmethyl)-1,4,7,10-tetraazacyclododecane able to form complexes with radioisotopes and a carboxyl terminal that connects to amino acids, peptides or proteins. Thus the radioisotopes are attached to specific tissues by identification of specific biological molecules. The specific binding of the radioisotopes to the tissues is achieved and the accuracy of nuclear medicine imaging is increased.

It is another object of the present invention to provide a contrast agent precursor having a 2-nitroimidazole group that is able to retain in hypoxic cells of living organisms. Thus radioisotopes that form complexes with the contrast agent precursor are taken up by the hypoxic cells and this helps the following signal detection and image capture.

It is a further object of the present invention to provide a method for preparing a contrast agent precursor that not only solves emulsion problem generated but also improves the purity of the product during purification of the intermediate product, 1,4,7-Tris(tert-butoxycarbonylmethyl)-1,4,7,10-tetraazacyclododecane-10-N-[6-(2-nitroimidazole)hexyl] acetamide.

It is a further object of the present invention to provide a method for preparing a contrast agent precursor that solves the problem of residual trifluoroacetic acid during purification of the final product 1,4,7-Tris(carbonylmethyl)-1,4,7,10-tetraazacyclo-dodecane-10-N-[6-(2-nitroimidazole) hexyl]acetamide (hereafter called DOTA-NI). Besides the improved purification yield, the method also avoids possible side effects on the living organisms caused by the following applications of the contrast agent.

In order to achieve the above objects, a contrast agent precursor according to the present invention includes a 1,4,7-Tris(carbonylmethyl)-1,4,7,10-tetraazacyclododecane connected to a 2-nitroimidazole/or derivatives and having a carboxyl terminal bonded with specific amino acids, peptides or proteins and a tetraaza terminal that forms complexes with radioisotopes. Thus the contrast agent precursor can be used to prepare a contrast agent has a specificity to hypoxic tissues and effective retention in the hypoxic tissues. The contrast agent not only can be used to get images of pathological tissues as an aid in the clinical diagnosis but also can be applied to the follow-up examination after treatment. Thus the contrast agent has a great potential in evaluation of diagnosis and prognosis of malignant tumors.

A method for preparing a contrast agent precursor according to the present invention includes a plurality of steps. First take 1,4,7,10-tetraazacyclododecane to react with tert-butyl bromoacetate and perform a first purification reaction to get 1,4,7-Tris(tert-butoxycarbonylmethyl)-1,4,7,10-tetraazacyclododecane. Then carry out a coupling reaction of 1,4,7-Tris(tert-butoxycarbonylmethyl)-1,4,7,10-tetraazacyclododecane with 6-[(2-nitroimidazole)hexyl]chloroacetamide and perform a second purification reaction to get 1,4,7-Tris(tert-butoxycarbonylmethyl)-1,4,7,10-tetraazacyclododecane-10-N-[6-(2-nitroimidazole)hexyl]acetamide. Next perform a deprotection reaction of 1,4,7-Tris(tert-butoxycarbonylmethyl)-1,4,7,10-tetraazacyclododecane-10-N-[6-(2-nitroimidazole)hexyl]acetamide and carry out a third purification reaction to get (1,4,7-Tris(carbonylmethyl)-1,4,7,10-tetraazacyclododecane-10-N-[6-(2-nitroimidazole)hexyl]acetamide.

In the step of taking 1,4,7,10-tetraazacyclododecane to react with tert-butyl bromoacetate, a catalyst is added and the reaction is carried out in an dimethylacetamide solution. The catalyst is sodium acetate. The reaction temperature is room temperature and the reaction time is 5 days.

During the first purification reaction, recrystallization is performed by using alcohol in a chloroform solution.

The coupling reaction is carried out in an acetonitrile solution and a catalyst is added. The catalyst is potassium carbonate.

In the second purification reaction, first add saturated sodium chloride solution and then extract with water and dichloromethane.

During the deprotection reaction, a deprotecting agent including trifluoroacetic acid (TFA), thioanisole and water is used. The reaction temperature is room temperature and the reaction time is 24 hours.

In the third purification reaction, use ether and dichloromethane for extraction and add hydrogen chloride in ether for removal of trifluoroacetic acid. Then carry out recrystallization by dichloromethane in an acetonitrile solution.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 3 is a flow chart showing steps of a method for preparing an embodiment according to the present invention.

DETAILED DESCRIPTION OF THE PREFERRED EMBODIMENT

In order to learn features and functions of the present invention, please refer to the following embodiments and descriptions in details.

The present invention provides a contrast agent precursor and a method for preparing the same. The contrast agent precursor has tissue-specificity and effective retention in hypoxic tissue with radioisotopes. Not only the detection efficiency of nuclear medicine imaging is improved, the tissue specificity, labeling accuracy and detection sensitivity of the contrast agent are also increased.

Figure 1:
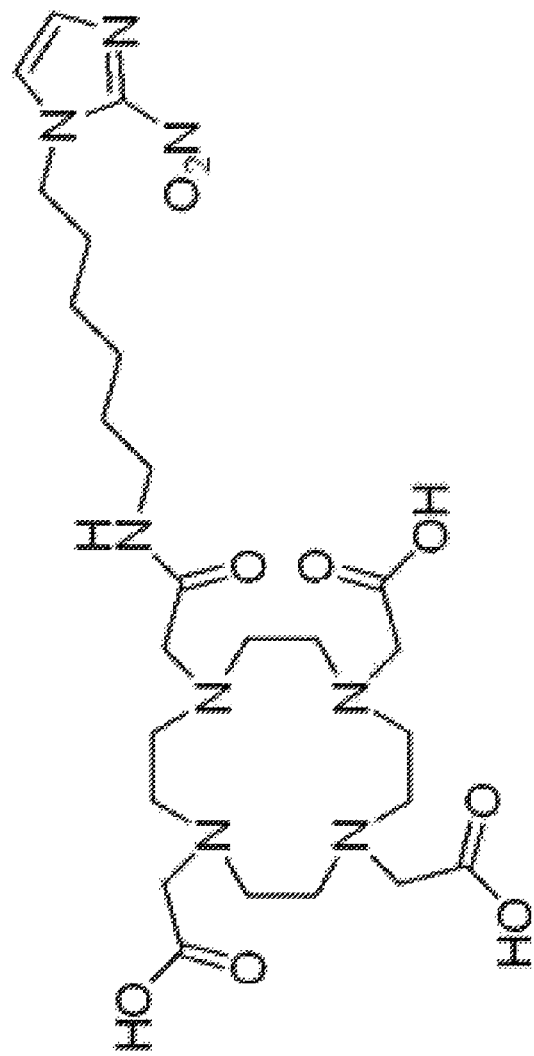
FIG. 1 shows a chemical structure of an embodiment according to the present invention.

Refer to FIG. 1, a chemical structure of a contrast agent precursor according to the present invention, 1,4,7-Tris(carbonylmethyl)-1,4,7,10-tetraazacyclododecane-10-N-[6-(2-nitroimidazole)hexyl]acetamide (hereafter called DOTA-NI), is revealed. The DOTA-NI includes a long-chain alkyl group, a 2-nitroimidazole and a chelate-1,4,7-Tris(carbonylmethyl)-1,4,7,10-tetraazacyclododecane. The 2-nitro-imidazole increases lipid solubility of DOTA-NI and helps the compound to pass through the cell membrane. The 1,4,7-Tris(carbonylmethyl)-1,4,7,10-tetraazacyclododecane that forms a complex with a radioisotope is connected to an amino acid, a peptide or a protein.

After entering the cell, the nitro group of 2-nitroimidazole is reduced into amine by Xanthine oxidase. Under normoxic conditions, the amine group is oxidized into the nitro group again and able to be out of the cell. On the other hand, the amine group of 2-nitroimidazole is unable to cross the membrane and retained in the cell due to increased polarity in the hypoxic cell.

In other words, 2-nitroimidazole is released from the cells after oxidation and reduction reactions in normoxic cells while 2-nitroimidazole is retained in the cells once the cells are under hypoxia. Thus 2-nitroimidazole can be used to differentiate hypoxic versus normoxic tissue. After connecting with radioactive isotopes, 2-nitroimidazole and derivatives are used as imaging agents with good performance owing to their long retention time in hypoxic tissues.

Figure 2:
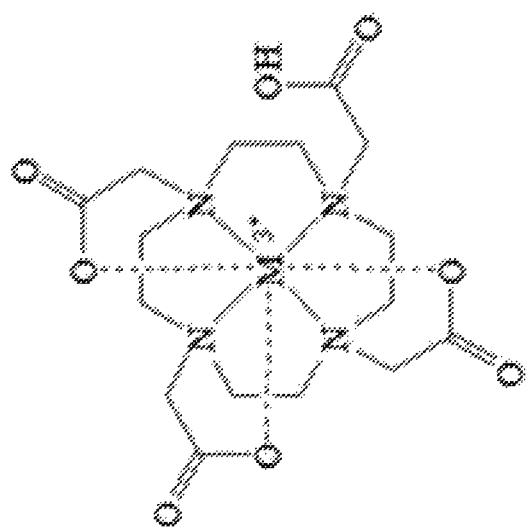
FIG. 2 shows a chemical structure of a complex compound of an embodiment according to the present invention.
Figure 2:
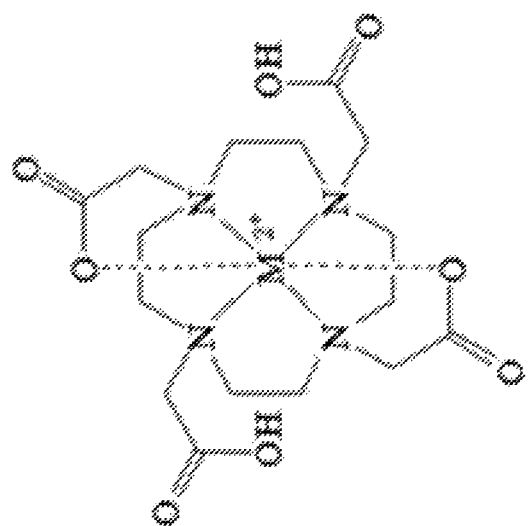

The contrast agent precursor includes a 1,4,7-Tris(carbonylmethyl)-1,4,7,10-tetraazacyclododecane that forms a stable complex with a radioisotope by a tetraaza terminal thereof. Thus the stable complex is used as a contrast agent. As shown in FIG. 2, $M^{2+}$ and $M^{3+}$ are bivalent and trivalent radioisotopes respectively. The radioisotope can be technetium-99m ($^{99m}Tc$), iodine-123 ($^{123}I$) or gallium-68 ($^{68}Ga$), most commonly used radioisotopes in nuclear medicine imaging. In the present invention, gallium-68 is preferred. Gallium-68 has a short half-life, 68 minutes and pharmacokinetics similar to peptides and small molecule drugs, featured on high distribution rate and clearance rate. Moreover, gallium-68 is the nucleotide with high probability of positron emission (89%) suitable for positron emission tomography (PET) that provides images with better quality.

1,4,7-Tris(carbonylmethyl)-1,4,7,10-tetraazacyclododecane also includes a carboxyl terminal that is covalently bonded to an amino acid, a peptide or a protein. Cellular transformation is usually accompanied by dysregulation of genes so that abnormal amount of protein is further synthesized. Thus there is a difference between the amount of specific protein expressed in normal cells and the amount of the specific protein expressed in cancer cells. Different representative genes are implicated in different cancers such as HER2 gene over-expression in breast cancer. Based on the fact mentioned above, a peptide that binds specifically to the specific protein can be found by review of literature on the tissue to be detected. Then the peptide is connected to the 1,4,7-Tris(carbonylmethyl)-1,4,7,10-tetraazacyclododecane. Thus radioisotopes can be delivered to the target tissue specifically. The contrast agent has high specificity and accuracy.

The contrast agent precursor DOTA-NI of the present invention has the 1,4,7-Tris(carbonylmethyl)-1,4,7,10-tetraazacyclododecane that is quickly binding to specific peptide and radioisotopes, and 2-nitroimidazole that enables the precursor to be retained in hypoxic tissues. After being connected to radioisotopes, the contrast agent formed is targeted to specific tumor tissues and retained in tumor cells. The images showing distribution of the contrast agent in the tumor tissues are obtained by detection of radioisotopes and used for monitoring the tumor tissues. Thus clinical diagnosis and prognosis of the tumors are more accurate.

Refer to FIG. 3, a method for preparing a contrast agent precursor according to the present invention includes the following steps.

Step S2: take 1,4,7,10-tetraazacyclododecane to react with tert-butyl bromoacetate and perform a first purification reaction to get 1,4,7-Tris(tert-butoxycarbonylmethyl)-1,4,7, 10-tetraazacyclododecane;

Step S4: carry out a coupling reaction of 1,4,7-Tris(tert-butoxycarbonylmethyl)-1,4,7,10-tetraazacyclododecane with 6-[(2-nitroimidazole)hexyl]-chloroacetamide and perform a second purification reaction to get 1,4,7-Tris(tert-butoxycarbonylmethyl)-1,4,7,10-tetraazacyclododecane-10-N-[6-(2-nitro imidazole)hexyl]acetamide;

Step S6: perform a deprotection reaction of 1,4,7-Tris (tert-butoxycarbonylmethyl)-1,4,7,10-tetraazacyclododecane-10-N-[6-(2-nitroimidazole)hexyl]acetamide and carry out a third purification reaction to get (1,4,7-Tris(carbonylmethyl)-1,4,7,10-tetraazacyclododecane-10-N-[6-(2-nitroimidazole)hexyl]acetamide.

Refer to the step S2 in FIG. 3, 1,4,7-Tris(tert-butoxycarbonylmethyl)-1,4,7,10-tetraazacyclododecane is obtained after 1,4,7,10-tetraazacyclododecane being reacted with tert-butyl bromoacetate as shown in the following equation 1:

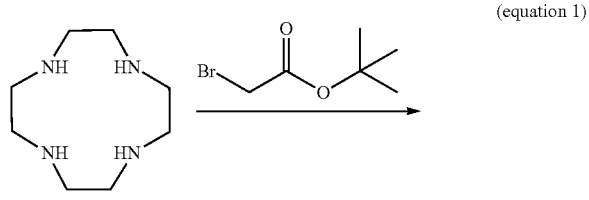

(equation 1)

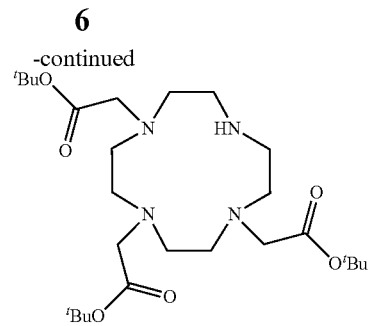

-continued

In the above reaction, sodium acetate is used as catalyst. The reaction occurs in a dimethylacetamide solution. The reactants are mixed slowly in an ice bath and the mixed solution is stirred at room temperature for several days. The optimal reaction time is, but not limited to, 5 days.

As to the first purification reaction, first the mixed solution in the step S2 is poured into water and added with sodium bicarbonate to get precipitate. Then filter the precipitate to obtain solid, add chloroform to dissolve the solid, and wash with water to get the organic layer. Next use anhydrous sodium sulfate for dehydration and vacuum evaporation for concentration. Perform the purification by using, but not limited to, a chloroform solution and recrystallization by alcohol.

Refer to the step S4, the coupling reaction between 1,4,7-Tris(tert-butoxycarbonylmethyl)-1,4,7,10-tetraazacyclododecane obtained in the step S2 and 6-[(2-nitroimidazole)hexyl]chloroacetamide for producing 1,4,7-Tris(tert butoxycarbonylmethyl)-1,4,7,10-tetraazacyclododecane-10-N-[6-(2-nitroimidazole)-hexyl]-acetamide is represented by the following equation 2.

(equation 2)

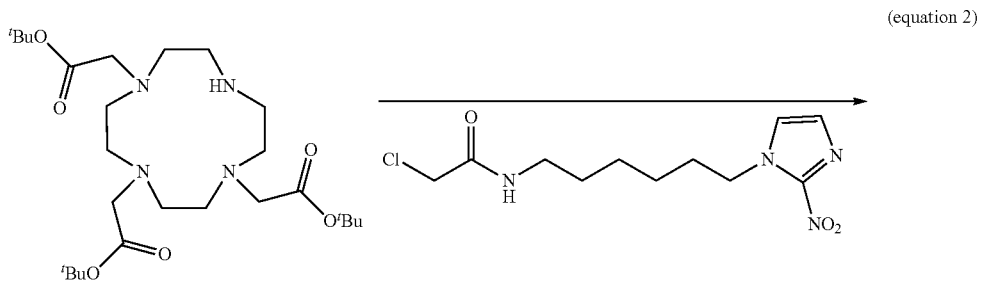

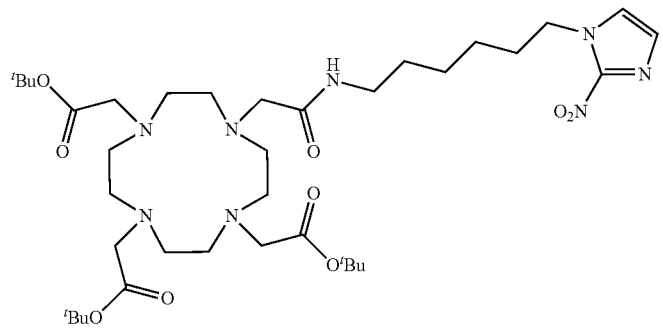

The catalyst used is potassium carbonate and the coupling reaction is carried out in an acetonitrile solution. First the reactants are stirred in an oil bath to get an initial solution and then add 6-[(2-nitroimidazole)hexyl]chloroacetamide into the mixed solution. The mixed solution is stirred constantly. Then the temperature of the mixed solution is increased and keep stirring the mixed solution.

The temperature of the oil bath used for the initial solution is ranging from 55° C. to 80° C. while 60° C. is preferred. The initial solution is stirred in the oil bath for 10 to 20 minutes and 15 minutes are preferred. Moreover, the temperature of the mixed solution being stirred is ranging from 55° C. to 80° C. while 60° C. is preferred and the stirring time is at least 14 hours. The temperature of the mixed solution is increased up to 90° C.~110° C. while 100° C. is preferred and keep stirring the mixed solution for 1 to 3 hours while 2 hours are preferred. The reaction conditions are not limited those mentioned above.

The second purification reaction includes the following steps. First filter the mixed solution obtained in the step S4. Then extract with water and dichloromethane and concentrate by vacuum evaporation to get an intermediate product. Before extraction, add saturated sodium chloride solution into the mixed solution to solve the emulsion problem occurred during purification process carried out by conventional techniques. The reaction conditions are not limited to those mentioned above.

Refer to the step S6, the deprotection reaction of 1,4,7-Tris(tert-butoxycarbonylmethyl)-1,4,7,10-tetraazacyclododecane-10-N-[6-(2-nitro-imidazole)hexyl]-acetamide that gets 1,4,7-Tris(carbonylmethyl)-1,4,7,10-tetraazacyclododecane-10-N-[6-(2-nitroimidazole)hexyl]acetamide is represented by the following equation 3.

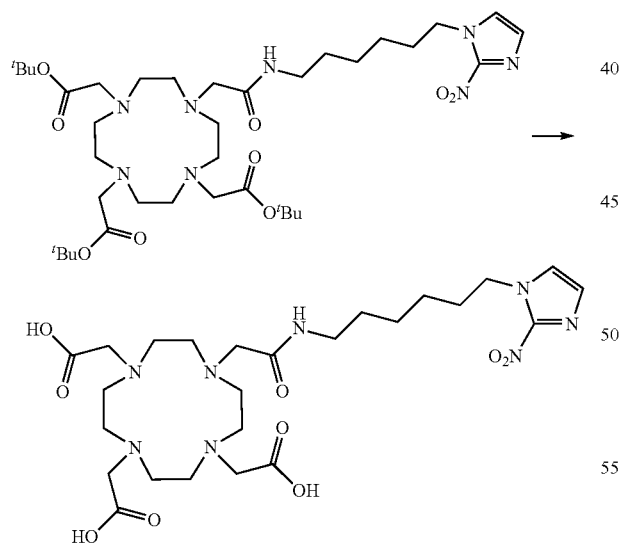

(equation 3)

The deprotection reaction is carried out by using a mixture of trifluoroacetic acid (TFA), thioanisole and water. The optimal reaction temperature is room temperature and the reaction time is 18-26 hours while 24 hours are preferred. The reaction conditions are not limited to those mentioned above.

In the third purification reaction, ether and dichloromethane are used for extraction and hydrogen chloride in ether is added for removal of trifluoroacetic acid. Then perform recrystallization by dichloromethane in an acetonitrile solution. After hydrogen chloride in ether being connected to trifluoroacetic acid, trifluoroacetic acid is separated from the target product in the form of hydrochloride salt. Thus the problem of the low yield rate generated during conventional removal of trifluoroacetic acid by ion-exchange resin can be solved. The problem of residual trifluoroacetic acid can also be improved. The reaction conditions are not limited to those mentioned above.

In order to learn techniques, features and functions of the present invention, please refer to the following embodiments.

Synthesis of 1,4,7-Tris(tert-butoxycarbonylmethyl)-1,4,7,10-tetraazacyclododecane Dissolve 2.0 g (11.6 mmol) starting material-1,4,7,10-tetraazacyclododecane in 25 ml dimethylacetamide and add 2.85 g (34.7 mmol) sodium acetate into the solution. Place the mixture in a 0 t ice bath, add 6.9 g (35.6 mmol) tert-butyl bromoacetate drop by drop, and stir the mixture at room temperature for 5 days. Then the mixture is poured into 125 ml water and add sodium bicarbonate into the mixed solution in batches. A solid is obtained after filtration and then is dissolved in 150 ml chloroform and washed with 75 ml water.

Next get the organic layer, and add anhydrous sodium sulfate for dehydration. After vacuum evaporation for concentration and dissolution in 20 ml chloroform, add 150 ml alcohol for recrystallization to get 3.83 g (64.0%) white solid product. The product is 1,4,7-Tris(tert-butoxycarbonylmethyl)-1,4,7,10-tetraazacyclododecane.

Analytic data of 1,4,7-Tris(tert-butoxycarbonylmethyl)-1,4,7,10-tetraazacyclododecane:

IR(KBr) v 3980 (NH), 1730 and 1720 (C=O), 1162 and 1140 (CO) cm$^{-1}$.

$^1$H NMR (CDCl$_3$) δ 10.05 (br, 1H, NH), 3.38 (s, 4H, C$\underline{H}_2$CO$_2$), 3.29 (s, 2H, C$\underline{H}_2$CO$_2$), 3.09 (s, 2H, NHCH$_2$C$\underline{H}_2$), 2.91-2.88 (m, 8H, C$\underline{H}_2$C$\underline{H}_2$NHCH$_2$CO$_2$), 1.46 (s, 27H, (CH$_3$)$_3$).

$^{13}$C NMR (CDCl$_3$) δ 171.13 and 170.24 (CO). 82.28 ($\underline{C}$(CH$_3$)$_3$), 58.80 (N$\underline{C}$H$_2$CO$_2$), 51.92 and 51.80 (N$\underline{C}$H$_2$CH$_2$N), 49.77 (N$\underline{C}$H$_2$CH$_2$NH), 48.13 (NCH$_2$$\underline{C}$H$_2$NH), 28.83 and 28.80 (C($\underline{C}$H$_3$)$_3$).

MS m/z 515 ((M+H)$^+$).

Synthesis of 1,4,7-Tris(tert-butoxycarbonylmethyl)-1,4,7,10-tetraazacyclododecane-10-N-[6-(2-nitroimidazole)hexyl]acetamide Dissolve 0.72 g (1.4 mmole) 1,4,7-Tris(tert-butoxycarbonylmethyl)-1,4,7,10-tetraazacyclododecane in 33.3 ml acetonitrile and add 0.51 g (3.7 mmole) potassium carbonate. Then the solution is stirred in an oil bath at 60° C. for 15 minutes to get an initial solution. Moreover, also dissolve 0.4 g (1.4 mmole) 6-[(2-nitroimidazole)hexyl]chloroacetamide in 33.3 ml acetonitrile to form another solution and then add this solution into the initial solution slowly drop by drop. It takes over 20 minutes to drop. Later stir the mixed solution at 60° C. overnight, heat the mixed solution to 100° C. and keep stirring for 2 hours. After diatomaceous-earth filtration, liquid obtained is concentrated by vacuum evaporation and is extracted thrice with 200 ml water and 200 ml dichloromethane. The organic layer obtained is dehydrated by anhydrous sodium sulfate and concentrated by vacuum evaporation to give a 0.89 g, 83.2% brown oily product, 1,4,7-Tris(tert-butoxycarbonylmethyl)-1,4,7,10-tetraazacyclododecane-10-N-[6-(2-nitroimidazole)hexyl]acetamide.

Analytic data of 1,4,7-Tris(tert-butoxycarbonylmethyl)-1,4,7,10-tetraazacyclododecane-10-N-[6-(2-nitroimidazole)hexyl]acetamide:

IR(neat) ν 3230 (NH), 1737 (C=O, ester), 1658 (C=O, amide), 1539 and 1366 (NO), 1158 and 1119 (CO) cm$^{-1}$.

$^1$H NMR (CDCl$_3$) δ 8.64 (t, 1H, NH), 7.15 and 7.14 (s, 2H, imi-H), 4.41 (t, 2H, C$\underline{H}_2$N), 3.27 (t, 2H, NHC$\underline{H}_2$), 3.23 and 3.04 (s, 6H, C$\underline{H}_2$CO$_2$), 2.88-2.87 (m, 8H, C$\underline{H}_2$CH$_2$NHCH$_2$CO$_2$), 2.72 (s, 2H, NHCH$_2$C$\underline{H}_2$), 2.51 (s, 2H, NHC$\underline{H}_2$CH$_2$), 1.92-1.81 (m, 2H, C$\underline{H}_2$CH$_2$N), 1.44 (s, 27H, (CH$_3$)$_3$), 1.38 (m, 2H, C$\underline{H}_2$CH$_2$CH$_2$CH$_2$N).

$^{13}$C NMR (CDCl$_3$) δ 172.66 and 171.26 (CO), 128.93 and 126.57 (imi-C), 81.61 ($\underline{C}$(CH$_3$)$_3$), 58.85 (N$\underline{C}$H$_2$CO$_2$), 57.36 ($\underline{C}$H$_2$CONH), 55.48 and 54.03 (N$\underline{C}$H$_2$$\underline{C}$H$_2$N), 53.13 (N$\underline{C}$H$_2$CH$_2$NH), 52.66 (NCH$_2$$\underline{C}$H$_2$NH), 50.83 (CH$_2$N), 39.61 (NHCH$_2$), 31.07 ($\underline{C}$H$_2$CH$_2$N), 30.25 (NHCH$_2$$\underline{C}$H$_2$), 28.83 (C($\underline{C}$H$_3$)$_3$), 27.00 ($\underline{C}$H$_2$CH$_2$CH$_2$N), 26.66 ($\underline{C}$H$_2$CH$_2$CH$_2$CH$_2$N).

MS m/z 768 ((M+H)$^+$).

Synthesis of 1,4,7-Tris(carbonylmethyl) 1,4,7,10-tetraazacyclododecane-10-N-[6-(2-nitroimidazole)hexyl]acetamide (DOTA-NI Take 1.66 g (2.16 mmole) 1,4,7-Tris(tert-butoxycarbonylmethyl)-1,4,7,10-tetraazacyclododecane-10-N-[6-(2-nitroimidazole)hexyl]acetamide, add 1.00 ml cocktail of deprotective reagents including 95% TFA, 2.5% thioanisole and 2.5% water and stir the solution at room temperature for 1 day. Extract three times with ether after vacuum evaporation. Take a part insoluble in ether and extract three times with dichloromethane and then extract three times with ether again. Take a part insoluble in ether and extract three times with dichloromethane again. Next add hydrogen chloride in ether and stir the mixture for 1 hour. Add 10 ml acetonitrile after vacuum evaporation and add 100 ml dichloromethane for recrystallization. Then place under vacuum for 1 day for dehydration to get a 0.80 g, 61.4% light brown solid. That's 1,4,7-Tris(carbonylmethyl)-1,4,7,10-tetraazacyclododecane-10-N-[6-(2-nitro-imidazole)hexyl]acetamide (DOTA-NI).

Analytic data of DOTA-NI:

IR(KBr) ν 3401 (CO$_2$H), 1733 (C=O, acid), 1672 (C=O, amide), 1537 and 1362 (NO) cm$^{-1}$.

$^1$H NMR ((CD$_3$)$_2$SO) δ 8.82 (br, 1H, NH), 7.68 and 7.11 (d, 2H, imi-H), 4.32 (t, 2H, C$\underline{H}_2$N), 4.13 (t, 2H, NHC$\underline{H}_2$), 4.06-3.81 (s, 6H, C$\underline{H}_2$CO$_2$), 3.78-3.40 (m, 8H, C$\underline{H}_2$CH$_2$NHCH$_2$CO$_2$), 3.36-2.61 (m, 2H, NHCH$_2$C$\underline{H}_2$), 1.69 (t, 2H, NHC$\underline{H}_2$CH$_2$), 1.57-1.32 (m, 2H, C$\underline{H}_2$CH$_2$N), 1.31-0.83 (m, 2H, C$\underline{H}_2$CH$_2$CH$_2$CH$_2$N).

$^{13}$C NMR ((CD$_3$)$_2$SO) δ 171.23, 167.78, 165.23 and 164.46 (CO), 127.76 (imi-C), 54.13 (N$\underline{C}$H$_2$CO$_2$), 53.72 ($\underline{C}$H$_2$CONH), 52.09 (N$\underline{C}$H$_2$$\underline{C}$H$_2$N), 50.47 (N$\underline{C}$H$_2$CH$_2$NH), 49.04 (NCH$_2$$\underline{C}$H$_2$NH), 48.03 (CH$_2$N), 47.53 (NHCH$_2$), 29.23 ($\underline{C}$H$_2$CH$_2$N), 28.15 (NHCH$_2$$\underline{C}$H$_2$), 25.39 ($\underline{C}$H$_2$CH$_2$CH$_2$N), 25.03 ($\underline{C}$H$_2$CH$_2$CH$_2$CH$_2$N).

MS m/z 637 ((M+HCl)$^+$).

In summary, a contrast agent precursor and a method for preparing the same according to the present invention not only solves the emulsion problem occurred during conventional purification of intermediate but also provides a solution to the problem of residual trifluoroacetic acid in the final product DOTA-NI. The yield rate and the quality of the product are also improved. The possible adverse effects of the contrast agent on living organisms are also minimized.

DOTA-NI prepared by the method of the present invention is formed by 1,4,7-Tris(carbonylmethyl)-1,4,7,10-tetraazacyclododecane connected to both the peptide and the radioisotope at the same time. The preparation efficiency of the radioisotope-labeled peptide is improved for more rapid results in clinical tests. Moreover, tissue specific peptide is selected to use to make the contrast agent have high specificity. The contrast agent is further retained in hypoxic tissues based on the biochemical property of 2-nitroimidazole in living organisms, especially in tumor tissues with hypoxia. The present contrast agent is a breakthrough in nuclear medicine imaging.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A contrast agent precursor, 1,4,7-Tris(carbonylmethyl)-1,4,7,10-tetraazacyclododecane-10-N-[6-(2-nitroimidazole)hexyl]acetamide, is represented by the following structural formula:

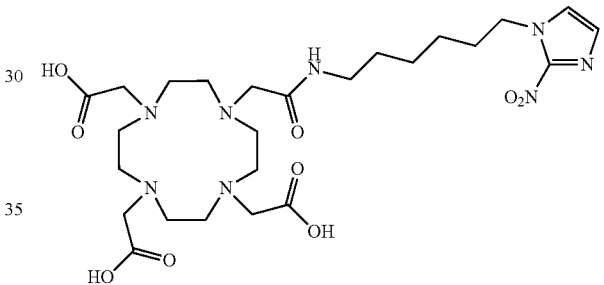

2. A method for preparing a contrast agent precursor comprising the steps of:
taking 1,4,7,10-tetraazacyclododecane to react with tert-butyl bromoacetate and performing a first purification reaction to get 1,4,7-Tris(tert-butoxycarbonylmethyl)-1,4,7,10-tetraazacyclododecane;
carrying out a coupling reaction of 1,4,7-Tris(tert-butoxycarbonylmethyl)-1,4,7,10-tetraazacyclododecane with 6-[(2-nitroimidazole)hexyl]chloroacetamide and performing a second purification reaction to get 1,4,7-Tris(tert-butoxycarbonylmethyl)-1,4,7,10-tetraazacyclododecane-10-N-[6-(2-nitroimidazole)hexyl]acetamide; and
performing a deprotection reaction of 1,4,7-Tris(tert-butoxycarbonylmethyl)-1,4,7,10-tetraazacyclododecane-10-N-[6-(2-nitroimidazole)hexyl]acetamide and carrying out a third purification reaction to get 1,4,7-Tris(carbonylmethyl)-1,4,7,10-tetraazacyclododecane-10-N-[6-(2-nitroimidazole)hexyl]acetamide.

3. The method as claimed in claim 2, wherein in the step of taking 1,4,7,10-tetraazacyclododecane to react with tert-butyl bromoacetate, a catalyst is added and the reaction is carried out in an dimethylacetamide solution; the catalyst is sodium acetate; reaction temperature is room temperature and reaction time is 5 days.

4. The method as claimed in claim 2, wherein recrystallization is carried by using alcohol in a chloroform solution during the first purification reaction.

5. The method as claimed in claim 2, wherein the coupling reaction is carried out in an acetonitrile solution and a catalyst is added; the catalyst is potassium carbonate.

6. The method as claimed in claim 2, wherein saturated sodium chloride solution is added first and then water and dichloromethane are used for extraction in the second purification reaction.

7. The method as claimed in claim 2, wherein a deprotecting agent including trifluoroacetic acid (TFA), thioanisole and water is used during the deprotection reaction; reaction temperature is room temperature and reaction time is 24 hours.

8. The method as claimed in claim 7, wherein in the third purification reaction, ether and dichloromethane are used for extraction and hydrogen chloride in ether is added for removal of trifluoroacetic acid, then recrystallization is carried out by dichloromethane in an acetonitrile solution.

\* \* \* \* \*